(12) United States Patent
Edgren et al.

(10) Patent No.: US 6,365,183 B1
(45) Date of Patent: Apr. 2, 2002

(54) METHOD OF FABRICATING A BANDED PROLONGED RELEASE ACTIVE AGENT DOSAGE FORM

(75) Inventors: David E. Edgren, El Granada; Patrick S.-L. Wong, Burlingame; Francisco Jao, San Jose; Yolanda M. Puga, Morgan Hill, all of CA (US)

(73) Assignee: ALZA Corporation, Mountain View, CA (US)

( * ) Notice: Subject to any disclaimer, the term of this patent is extended or adjusted under 35 U.S.C. 154(b) by 0 days.

(21) Appl. No.: 09/274,648

(22) Filed: Mar. 23, 1999

Related U.S. Application Data

(60) Provisional application No. 60/084,646, filed on May 7, 1998.

(51) Int. Cl.[7] ................................................. A61K 9/22
(52) U.S. Cl. ..................... 424/468; 424/464; 424/467
(58) Field of Search ................................ 424/400, 464, 424/467, 468

(56) References Cited

U.S. PATENT DOCUMENTS

| | | | |
|---|---|---|---|
| 2,052,376 A | 8/1936 | Zellers | |
| 2,962,851 A | 12/1960 | Hall | |
| 4,290,426 A | 9/1981 | Luschen et al. | |
| 4,327,725 A | 5/1982 | Cortese et al. | |
| 4,503,031 A | 3/1985 | Glassman | |
| 4,792,448 A | 12/1988 | Ramade | |
| 4,824,677 A | * 4/1989 | Shah et al. | 424/467 |
| 4,839,177 A | 6/1989 | Colombo et al. | |
| 4,915,950 A | 4/1990 | Miranda et al. | |
| 5,023,088 A | 6/1991 | Wong et al. | |
| 5,256,440 A | 10/1993 | Appel et al. | |
| 5,266,332 A | 11/1993 | Dong et al. | |
| 5,326,570 A | 7/1994 | Rudnic et al. | |
| 5,422,123 A | 6/1995 | Conte et al. | |
| 5,520,929 A | * 5/1996 | Makino et al. | 424/467 |
| 5,534,263 A | 7/1996 | Wong et al. | |
| 5,667,804 A | 9/1997 | Wong et al. | |

FOREIGN PATENT DOCUMENTS

| | | |
|---|---|---|
| DE | 43 41 548 | 6/1995 |
| EP | 0 088 556 | 9/1983 |
| EP | 0 403 214 | 12/1990 |

OTHER PUBLICATIONS

Conte, U., et al., Journal of Controlled Release, 26 (1993), pp. 39–47, "Mulit–Layered hydrophilic matrices as constant release devices".

* cited by examiner

*Primary Examiner*—Jose' G. Dees
*Assistant Examiner*—Konata M. George
(74) *Attorney, Agent, or Firm*—Andrea G. Reister; Covington & Burling (57) ABSTRACT

The present invention is directed to an active agent dosage form and methods of its fabrication which is useful for the prolonged delivery of an active agent formulation to a fluid environment of use. The active agent dosage form is a matrix that has on its surface one or more insoluble bands located in complementary grooves. The invention is also directed to articles of manufacture, methods and systems for fabricating the active agent dosage form.

30 Claims, 6 Drawing Sheets

FIG. 11 methods of fabricating a banded
prolonged release active agent
dosage form

METHOD OF FABRICATING A BANDED PROLONGED RELEASE ACTIVE AGENT DOSAGE FORM

This application claims priority under 35 U.S.C. § 119(e) to provisional application No. 60/084,646, filed May 7, 1998, the entirety of which is incorporated herein by reference.

FIELD OF THE INVENTION

The present invention is related to the prolonged delivery of an active agent. More particularly, it is directed to an improved method of making a banded active agent dosage form which is useful for delivering a beneficial agent to a fluid environment of use.

BACKGROUND OF THE INVENTION

Tablets, capsules, caplets and many other types of devices have been used for dispensing a beneficial agent to a fluid environment of use. Easy manufacture of a device that provides for prolonged delivery of an active agent in a controlled and predictable manner continues to be a goal, especially in the area of drug delivery.

U.S. Pat. No. 4,290,426 to Luschen et al describes a cylindrical dispenser for releasing a beneficial agent into a fluid environment at a rate that is governed by the fluid-induced relaxation of a polymeric agent contained within the dispenser. The cylindrical dispenser includes an impermeable container that has within it a reservoir and a passageway from the reservoir to the exterior of the container. The reservoir contains a polymer and a beneficial agent. The polymer imbibes fluid from the environment and thereby undergoes relaxation, releasing the beneficial agent from the device. The amount of agent released is dependent on the rate of relaxation of the polymer over time.

Coated dosage forms have also been suggested for delivery of a controlled amount of a beneficial agent over a prolonged period of time. U.S. Pat. No. 5,256,440 describes a process for producing a film coated dosage form. A continuous groove is inscribed in a dosage form core. A latex film is coated onto the core, the groove defining a fixed zone and a detachable zone for the film. The detachable portion of the latex film detaches when it is exposed to the environment of use, thereby exposing a discrete portion of the dosage form core surface. The remainder of the film remains attached to the dosage form core. The exposed portion of the dosage form surface erodes and releases active agent to the environment of use.

Coated tablets for constant and prolonged drug release are described by Conte et al in *J. Controlled Release*, Vol. 26, (1993) pages 39–47. These GEOMATRIX™ Systems are swellable matrices that are coated or tabletted with polymeric barrier layers. Release performances of the systems are modulated as a result of the restriction of the releasing surface by the polymeric barrier layer coatings. As the extent of coating of the system's surface is increased, the release kinetics of the system shift toward constant release. These systems are further described in U.S. Pat. No. 4,839,177 to Colombo et al.

U.S. Pat. No. 5,534,263 describes a banded dosage form which is useful for the sustained delivery of an active agent formulation to a fluid environment of use. The active agent dosage form is a matrix that has on its surface two or more insoluble bands. The dosage form described provides significant advantages over other prior art devices for the sustained delivery of an active agent.

SUMMARY OF THE INVENTION

It has been observed that banded devices such as those described in U.S. Pat. No. 5,534,263 ('263 patent), which is incorporated herein by reference in its entirety, have significant advantages for prolonged delivery of an active agent formulation to a fluid environment of use. It has now been discovered that if the active agent formulation matrix is provided with at least one groove, prior to the banding process described in the '263 patent, the groove can be used as a register to orient the dosage form during the banding process. Additionally, the groove allows for more uniform deposition of the banding material. In that manner, improved dosage forms are provided and savings and manufacturing advantages are achieved.

Accordingly, the present invention is directed to an improved method and system for manufacturing banded dispensing devices, to improved articles of manufacture, and to components that facilitate manufacture of the devices.

In one aspect, the invention comprises an active agent dosage form for the prolonged delivery of an active agent formulation to a fluid environment of use, the dosage form comprising an active agent formulation matrix having at least one groove circumscribing a portion of the surface thereof and an insoluble band positioned in the groove.

In another aspect the invention comprises a blank for formation of an active agent dosage form for controlled delivery of an active agent, the blank comprising an active agent formulation matrix having at least one groove circumscribing a portion of the surface thereof.

In a further aspect the invention comprises a banding system for fabricating an active agent dosage form comprising means for orienting a blank having a groove and means for forming a band in the groove.

The invention comprises the following characteristics and features, either alone or in combination with one or more of each other:

An active agent dosage form for the prolonged delivery of an active agent formulation to a fluid environment of use, the dosage form comprising an active agent formulation matrix having at least one groove circumscribing a portion of the surface thereof and an insoluble band located in the groove; the dosage form wherein the groove has the shape of a notch; the dosage form wherein the groove has a continuous concave shape; the dosage form wherein the depth of the groove is between 0.1 and 3 mm; the dosage form wherein the width of the groove is between 0.5 and 10 mm; the dosage form wherein the outer surface and bands are coated to form a smooth, exterior surface; and the dosage form having more than one groove circumscribing a portion of the surface thereof and an insoluble band located in each groove.

A blank for formation of a pharmaceutical dosage form for controlled delivery of an active agent, the blank comprising an active agent formulation matrix having at least one groove circumscribing a portion of the surface thereof; the blank wherein the groove has the shape of a notch; the blank wherein the groove has a continuous concave shape; the blank wherein the depth of the groove is between 0.1 and 3 mm; the blank wherein the width of the groove is between 0.5 and 10 mm; the blank wherein the groove functions as a location register; the blank wherein the groove is adapted to cooperate with a printing means; the blank wherein the groove is adapted to cooperate with a printing means having a latex source; and the blank wherein the groove is adapted to cooperate with a printing means having a latex source selected from acrylate esters.

A system for fabricating the dosage form from a blank comprising an active agent formulation matrix and at least one groove on the surface thereof, the system comprising means for orienting the blank by means of a groove in the blank, and means for forming a band in a groove; the system including means for transporting the blank; the system wherein the means for orienting the blank includes means registering with one or more of the grooves on the blank; the system wherein the means for orienting the blank includes a rotatable wheel; the system wherein the band forming material comprises a latex of acrylate polymers; the system wherein the acrylate polymers comprise copolymers of ethylacrylate and methylmethacrylate; and the system wherein the means for forming a band in a groove comprises printing means.

A method of preparing an active agent dosage form for the prolonged delivery of an active agent formulation to a fluid environment of use, the dosage form comprising an active agent formulation matrix having at least one groove circumscribing a portion of the surface thereof and a band of insoluble material positioned in the groove, the method comprising forming a blank having a groove corresponding to a desired location of the insoluble band, and coating the groove with the insoluble material.

DESCRIPTION OF THE DRAWINGS

The figures are not drawn to scale, but are set forth to illustrate various embodiments of the invention. Like numbers refer to like structures.

DETAILED DESCRIPTION OF THE INVENTION

The present invention provides a delivery device and articles of manufacture and systems and methods for fabrication of the device, the device being useful for the prolonged delivery of an active agent formulation to a fluid environment of use.

DEFINITIONS

The phrase "prolonged delivery" intends a period of delivery that lasts for several hours to about 24 hours, usually up to about 20 hours, and often between about 3 and 16 hours.

By "insoluble" is intended a material that will not dissolve, degrade or erode in the environment of use during the delivery period.

By "apply" or "applied" or "application" is intended the deposition of insoluble material, in liquid or in molten form, onto the active agent formulation matrix. A variety of techniques may be used to apply the insoluble material, including but not limited to Gravure-type printing, extrusion coating, screen coating, brush coating, spraying, painting, and the Capsealer process developed by TAIT Design & Machine Co., Manheim, Pa. and the system developed and sold by Shionogi Qualicaps of Indianapolis, Ind., commonly referred to as the Quali-seal™ process. These systems can be used with modification of their usual capsule feed systems to accommodate the compressed tablet blanks typically used in the present invention.

The term "active agent formulation" intends the active agent or drug optionally in combination with pharmaceutically acceptable carriers and additional inert ingredients.

The term "active agent formulation matrix", as used herein, comprises the active agent formulation in combination with a hydrophilic polymeric material.

The "active agent dosage form" intends the active agent formulation matrix as defined above with one or more bands of an insoluble material applied onto its surface.

The term "blank" means an active agent formulation matrix formed without any band but with at least one groove circumscribing a portion of its surface. A blank may have more than one groove to facilitate placement of a plurality of bands contemplated herein.

As used herein, the terms "therapeutically effective" amount or rate refer to the amount or rate of the active agent needed to effect the desired pharmacologic, often beneficial, result.

The dispensing devices of the invention embody improvements over the dispensing devices described in U.S. Pat. No. 5,534,263 ("263 patent"), which is incorporated herein by reference. The dispensing devices of the invention find use, for example, in humans or other animals. The environment of use is a fluid environment and can comprise the stomach, the intestinal tract, or a body cavity such as the peritoneum or vagina. A single dispensing device or several dispensing devices can be administered to a subject during a therapeutic program.

The dispensing devices of the invention are fabricated by methods and with systems improved over that described in the '263 patent and the prior art. In prior methods, the dispensing devices were produced from cylindrical tablets having a uniformly continuous external surface without any grooves. In the banding equipment unbanded tablets were rotated at a printing station as banding material was applied to the external surface of the unbanded tablets. Bands were thus applied to the external surface and the band thickness resulted in a finished banded device having a non-uniform external surface as can be seen from the illustrations in the figures of the '263 patent. The unbanded tablets were rotated independently of the printing means and had the tendency to wobble as the bands were applied. This resulted in some of the bands being applied in a non-uniform manner, particularly around the edges, and with non-uniform band thickness. Such non-uniformity may affect the delivery profile of the active agent from the dispensing device and, as such, a less than optimal delivery device is produced.

It has now been discovered that if an indexing or register means is provided on the unbanded device prior to the banding operation, the banding means can be configured to cooperate with the indexing or register means to locate the unbanded device accurately at the location at which the insoluble band material is placed on the unbanded device during the banding operation. The indexing or register means may be provided by one or more grooves, formed on a portion of the external surface of the unbanded device, that cooperate with the banding means. Accordingly, bands can be applied with greater uniformity in location, width and thickness. This results in rejection of fewer dispensing devices for being out of specifications and also provides dispensing devices having optimal surface characteristics and active agent release profiles. The indexing or register means cooperates with the banding means to align the unbanded dispensing device during the banding operation.

The invention can best be understood with reference to the drawings.

Figure 1:
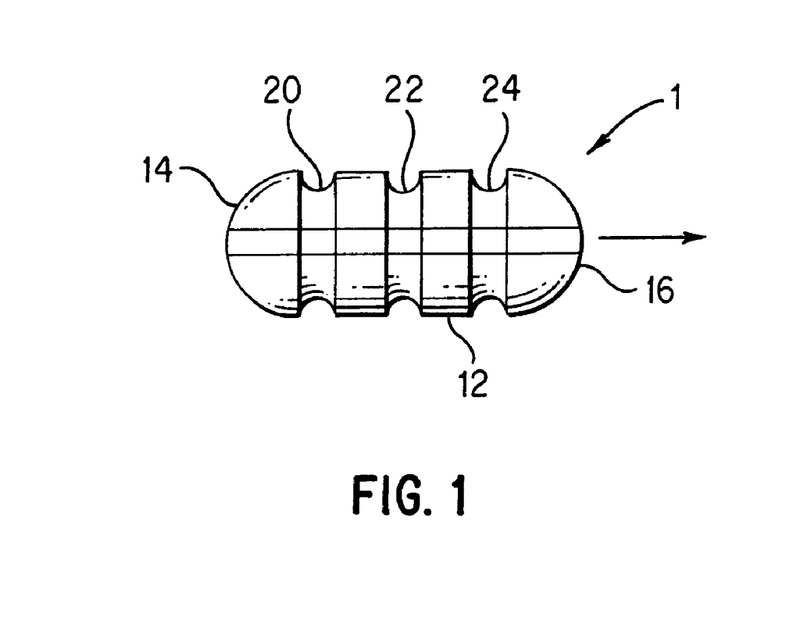
FIG. 1 is a side elevational view of one embodiment of a blank useful for fabrication of the delivery device of the present invention, the blank being in prepared form prior to printing of bands in the grooves on the surface of the blank.

FIG. 1 depicts, in side elevational view, one embodiment of the unbanded dispensing device, which henceforth will be referred to as a "blank". The blank is shown in prepared form prior to placement of the bands. Blank 1 is shown in FIG. 1 to comprise a cylindrically shaped active agent formulation matrix 12. The ends 14 and 16 of the matrix are preferably rounded and convex in shape in order to ensure ease of insertion into the environment of use. Grooves 20, 22 and 24 are formed in and circumscribe the exterior surface of the active agent formulation matrix 12. Multiple grooves are illustrated. However, it will be appreciated that the blank may be formed with only one groove or with more than one groove.

Figure 2:
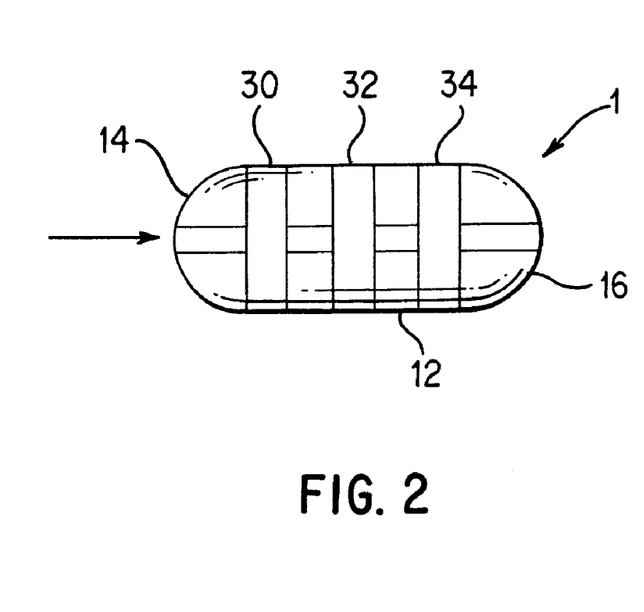
FIG. 2 illustrates the blank of FIG. 1 after the banding operation has been completed.

FIG. 2 shows blank 1 after the banding operation has been completed and bands 30, 32, and 34 have been formed in grooves 20, 22, and 24, respectively. That operation results in a delivery device that is suitable to be placed in the fluid environment of use and operate as described in the '263 patent. Because the bands have been placed in the grooves and generally will be configured to extend only to the outer surface of the blank, the outer surface of the delivery device will be quite smooth. Optionally, however, the completed device may be coated with a water-soluble film as described in the '263 patent. The active agent formulation matrix 12 between bands 30, 32 and 34 and at its ends 14 and 16 will erode when the delivery device is placed in the environment of use, thereby releasing active agent to the fluid environment of use.

Figure 3:
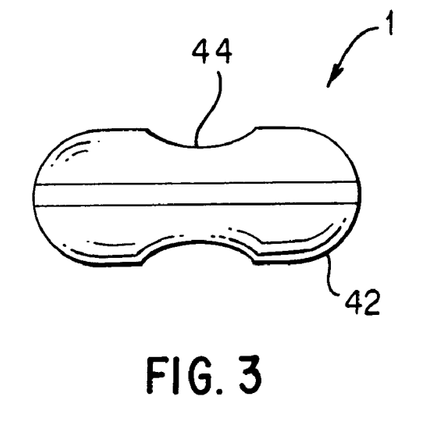
FIG. 3 is a side elevational view illustrating a particular embodiment of the blank of this invention having a groove formed as a concave surface.

FIG. 3 shows a blank 1 having a single groove 44, shaped as a concave surface, in the outer surface of active agent formulation matrix 42. While a single groove is illustrated, more than one groove may be provided depending on the number of bands that will be placed on the completed delivery device.

Figure 4:
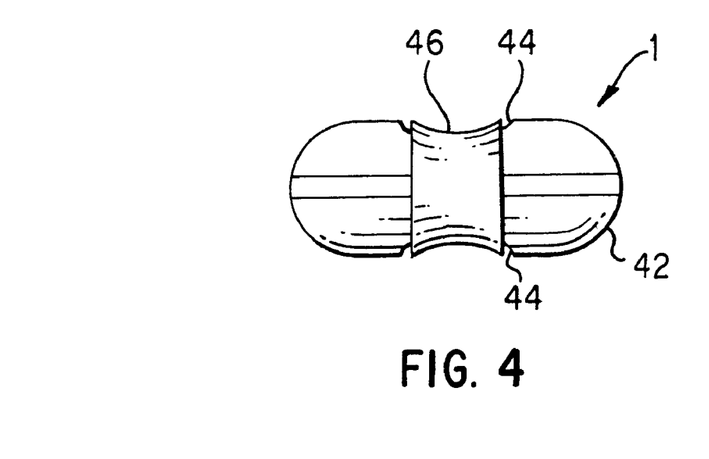
FIG. 4 illustrates the blank of FIG. 3 after the banding operation has been completed.

FIG. 4 shows blank 1 after the banding operation has been completed to form a completed delivery device. Groove 44 has been imprinted with band 46, which, as illustrated, has to some extent assumed the concave shape of groove 44. However, it is to be understood that band 46 may be formed with additional material to fill groove 44 to provide an external surface in the area of the groove that is level with the external surface of the active agent formulation matrix 42 outside of the banded area. As has been described previously, the banded dispensing device may be used in that configuration, or it may be optionally over-coated with a water-soluble film as described in the '263 patent. When placed in the environment of use, any optional over-coated water soluble film will dissolve, and the external surface of active agent matrix 42 not covered by band 46 will erode and release active agent. Erosion will continue and the exposed ends will separate from the banded portion of the device. Upon continued erosion, band 46 will separate from any remaining active agent formulation matrix and will thereafter be expelled from the fluid environment of use.

Figure 5:
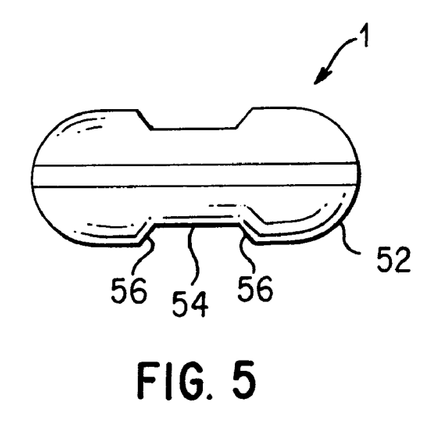
FIG. 5 is a side elevational view illustrating another embodiment of a blank of this invention having a groove formed as a notch.

FIG. 5 shows another embodiment of a blank 1 of the invention having a notched groove 54 formed with sloping sides 56. It is to be appreciated that sides 56 could be formed at other angles to the longitudinal axis of the active agent formulation matrix 52. For example, sides 56 could be at right angles to the longitudinal axis. The particular choice of shape will be made by one skilled in the art depending on application for which the dispensing device is intended to be used.

Figure 6:
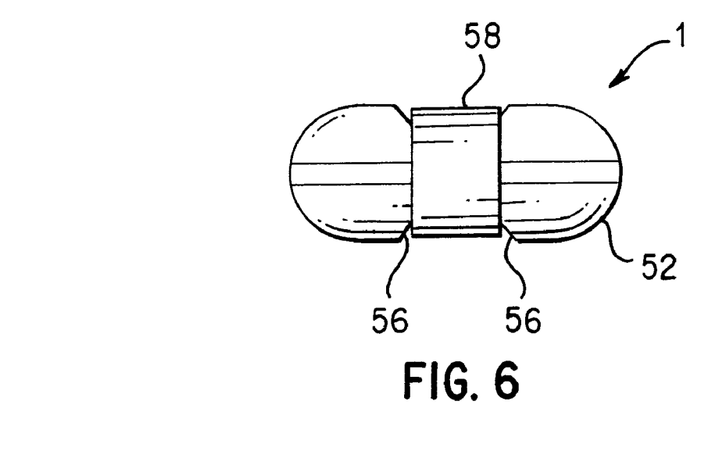
FIG. 6 illustrates the blank of FIG. 5 after the banding operation has been completed.

FIG. 6 shows the blank of FIG. 5 after the banding operation has been completed and a band 58 has been located in groove 54. The notched shape facilitates the application of a uniform thickness of material forming band 58, and may provide an external surface that is level with the surface of the active agent formulation matrix 52. More than one groove 54 can be provided as desired. The blank and delivery device can be utilized as described herein and in accordance with the teachings of the '263 patent.

The number, size, and placement of the insoluble bands that are applied onto the active agent formulation matrix may be varied to provide a desired drug delivery profile, in conjunction with design of the active agent formulation. For example, grooves of from about 0.1 mm to about 12 mm in width, preferably between about 0.5 and 10 mm, and most preferably between about 0.5 and 8 mm, may be formed into the blank, resulting in bands of approximately that width on the active agent formulation matrix surface. Typically, the grooves will be formed with a maximum depth of 0.1 mm to 3 mm, preferably 0.1 mm to 2 mm. However, for applications where there is significant swelling of the polymer matrix of the tablet, the depth of the groove may be greater to accommodate bands of increased thickness and strength. Between about 1 and 10 bands may be used, but generally between about 1 and 6 are affixed to the matrix. The bands may be placed close together (i.e., within about 0.5 mm of each other) or may be placed at opposite ends of the matrix (i.e., spaced about 8 to 12 mm apart).

The insoluble material may be any material that is nontoxic, biologically inert, nonallergenic and nonirritating to body tissue, and that maintains its physical and chemical integrity; that is, the bands do not erode or degrade in the environment of use during the dispensing period. Insoluble materials from which the bands may be prepared include, for example, polyethylene, polystyrene, ethylene-vinyl acetate copolymers, polycaprolactone and Hytrel® polyester elastomers (Du Pont). Additional banding materials include but are not limited to polysaccharides, cellulosics, powdered cellulose, microcrystalline cellulose, cellulose acetate, cellulose acetate pseudolatex (such as described in U.S. Pat. No. 5,024,842), cellulose acetate propionate, cellulose acetate butyrate, ethyl cellulose, ethyl cellulose pseudolatex (such as Surelease® as supplied by Colorcon, West Point, Pa. or Aquacoat™ as supplied by FMC Corporation, Philadelphia, Pa.), nitrocellulose, polylactic acid, poly- glycolic acid, polylactide glycolide copolymers, collagen, polycaprolactone, polyvinyl alcohol, polyvinyl acetate, polyethylene vinylacetate, polyethylene teraphthalate, polybutadiene styrene, polyisobutylene, polyisobutylene isoprene copolymer, polyvinyl chloride, polyvinylidene chloride-vinyl chloride copolymer, copolymers of acrylic acid and methacrylic acid esters, copolymers of methylmethacrylate and ethylacrylate, latex of acrylate esters (such as Eudragit® supplied by RöhmPharma, Darmstaat, Germany), polypropylene, copolymers of propylene oxide and ethylene oxide, propylene oxide ethylene oxide block copolymers, ethylenevinyl alcohol copolymer, polysulfone, ethylene vinylalcohol copolymer, polyxylylenes, polyamides, natural and synthetic waxes, paraffin, carnauba wax, petroleum wax, white or yellow bees wax, castor wax, candelilla wax, rice bran wax, microcrystalline wax, stearyl alcohol, cetyl alcohol, bleached shellac, esterified shellac, chitin, chitosan, silicas, polyalkoxysilanes, polydimethyl siloxane, polyethylene glycol-silicone elastomers, crosslinked gelatin, zein, electromagnetic irradiation crosslinked acrylics, silicones, or polyesters, thermally crosslinked acrylics, silicones, or polyesters, butadienestyrene rubber, glycerol ester of partially dimerized rosin, glycerol ester of partially hydrogenated wood rosin, glycerol ester of tall oil rosin, glycerol ester of wood rosin, pentaerythritol ester of partially hydrogenated wood rosin, pentaerythritol ester of wood rosin, natural or synthetic terpene resin and blends of the above.

Preferred banding materials include copolymers of acrylic acid and methacrylic acid esters, copolymers of methylmethacrylate and ethylacrylate, and latex of acrylate esters. Preferred copolymers include poly (butyl methacrylate, (2-dimethylaminoethyl)methacrylate, methyl methacrylate) 1:2:1, 150,000, sold under the trademark EUDRAGIT E; poly (ethyl acrylate, methyl methacrylate) 2:1, 800,000, sold under the trademark EUDRAGIT NE 30 D; poly (methacrylic acid, methyl methacrylate) 1:1, 135,000, sold under the trademark EUDRAGIT L; poly (methacrylic acid, ethyl acrylate) 1:1, 250,000, sold under the trademark EUDRAGIT L; poly (methacrylic acid, methyl methacrylate) 1:2, 135,000, sold under the trademark EUDRAGIT S; poly (ethyl acrylate, methyl methacrylate, trimethylammonioethyl methacrylate chloride) 1:2:0.2, 150,000, sold under the trademark EUDRAGIT RL; poly (ethyl acrylate, methyl methacrylate, trimethylammonioethyl methacrylate chloride) 1:2:0.1, 150,000, sold as EUDRAGIT RS. In each case, the ratio x:y:z indicates the molar proportions of the monomer units and the last number is the number average molecular weight of the polymer. An ethylacrylate methylmethylacrylate 2:1 copolymer latex is especially preferred.

The banding materials often are also formulated with plasticizers, and optionally with wetting agents, surfactants, opacifiers, colorants, flavorants, taste-masking agents, and the like. Examples of typical plasticizers are as follows: polyhydric alcohols, triacetin, polyethylene glycol, glycerol, propylene glycol, acetate esters, glycerol triacetate, triethyl citrate, acetyl triethyl citrate, glycerides, acetylated monoglycerides, oils, mineral oil, castor oil and the like. Triacetin presently is a preferred plasticizer. The plasticizers may be blended into the latex in amounts of 10–50 weight percent based on the weight of the latex. Preferably, 20–40 weight percent of plasticizer, based on the weight of the latex, may be utilized.

Tablets formed of the active agent formulation matrix are made by standard granulation and tabletting methods. The tablet tooling however is of particular design; it is made for use in the horizontal compression mode ("HCT"), such as described, for example, in *Remington's Pharmaceutical Sciences*, 14th Edition, pages 1660–1666. Tableting design is described in *Pharmaceutical Dosage Forms: Tablets*, Volume 2, Chapter 7, published by Marcel Dekker, Inc. Tooling is designed with embossment to form one or more grooves in the active agent formulation matrix as it is tabletted. The HCT tablets are compressed such that at least one continuous groove is embossed which lies in a plane perpendicular to the longitudinal axis of the tablet and circumscribes a portion of the external surface of the tablet. Dies and punches are fabricated with ridges that are located, shaped and sized to form the grooves in the blanks as the active agent formulation matrix is tabletted.

Fabrication of the completed delivery devices by banding the blanks of the invention may take place on tablet or caplet banding systems and in accordance with known banding processes as described generally below.

The grooved tablets formed in the tabletting operation are fed to a banding machine (Tait or Shinonogi capsealer). The tablets roll on the machine and when they reach the banding station, the printing wheel(s) transfers coating material (e.g., ethylacrylate methylmethacrylate 2:1 copolymer latex) into the groove(s). Typically, one printing wheel corresponding to each groove on the blank will be used. The width of the wheels is smaller than the width of the grooves so that the printing surface of the wheel rotates within the confines of the groove. The system continues to rotate while the water of the latex is subsequently dried in a current of warm air. The bands form within the grooves as the water is removed and the latex coalesces. The system is optionally given a final film overcoat to complete fabrication, as is described in the '263 patent. Bands of the resulting systems have clean, straight borders, defined by the borders of the embossed grooves and uniform thickness. Typically, the band edges will meet, or at least do not extend above, the external surface of the active agent formulation matrix, thus providing a smooth, continuous outer surface. While the invention is described with the printing means comprising a printing wheel for application of the banding material to the groove surface, it is understood that other printing apparatus known to those skilled in the art, such as jet-droplet printing, offset Gravure equipment, spray curtain printing, and the like, may be used as well.

A schematic of a banding system useful in the practice of the invention is illustrated in greater detail in FIGS. 7–10. As shown, the banding system comprises a source of blanks, typically a vibratory or rotary feed hopper 61; a transport mechanism to move blanks to the printing station, typically comprising a rotating transport table 62, or alternatively a linear conveyer, and a stationary table 63 upon which the blanks roll during processing; and one or more banding stations 64 having a printing means, typically including a source of banding material 65 and a printing wheel 66.

In the illustrated embodiment, the feed hopper 61 is positioned over table 62 that is adapted to rotate horizontally over stationary table 63. Table 62 is formed with a plurality of slots or openings 67 that are positioned linearly on respective radii of table 62 and are adapted to receive blanks from the feed hopper. For ease of illustration, a single feed hopper that feeds a plurality of slots 67 along a radius of table 62 is shown. Alternatively, individual feed hoppers for each circumferential set of openings might be used. Table 63 forms a stationary surface that supports the blanks as the blanks are transported to banding station 64. Openings 68, shown in FIGS. 9 and 10, in stationary table 63 are sized to be slightly smaller than openings 67 so that the blanks continue to be supported at the banding station. Openings 68 are sized to accommodate the printing means so that banding material can be applied to the grooves of the blank.

Figure 7:
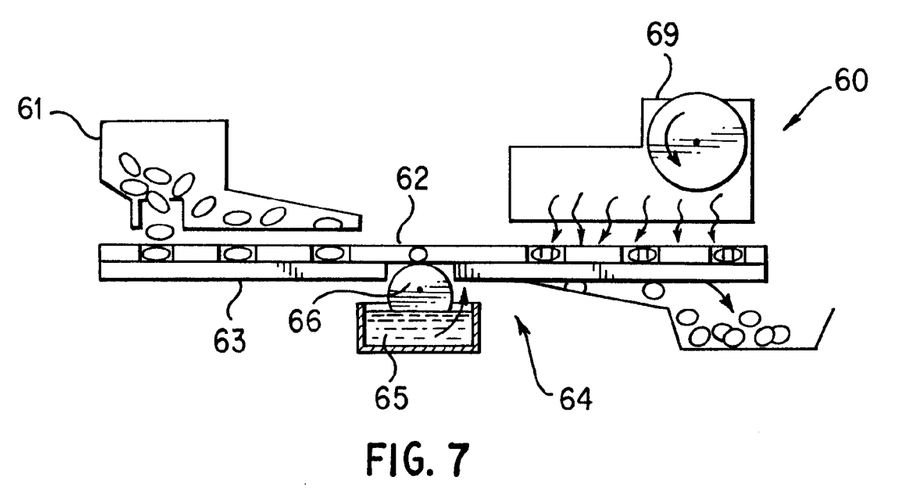
FIG. 7 is a side, elevational view schematically illustrating the major components of the banding system of the present invention.
Figure 8:
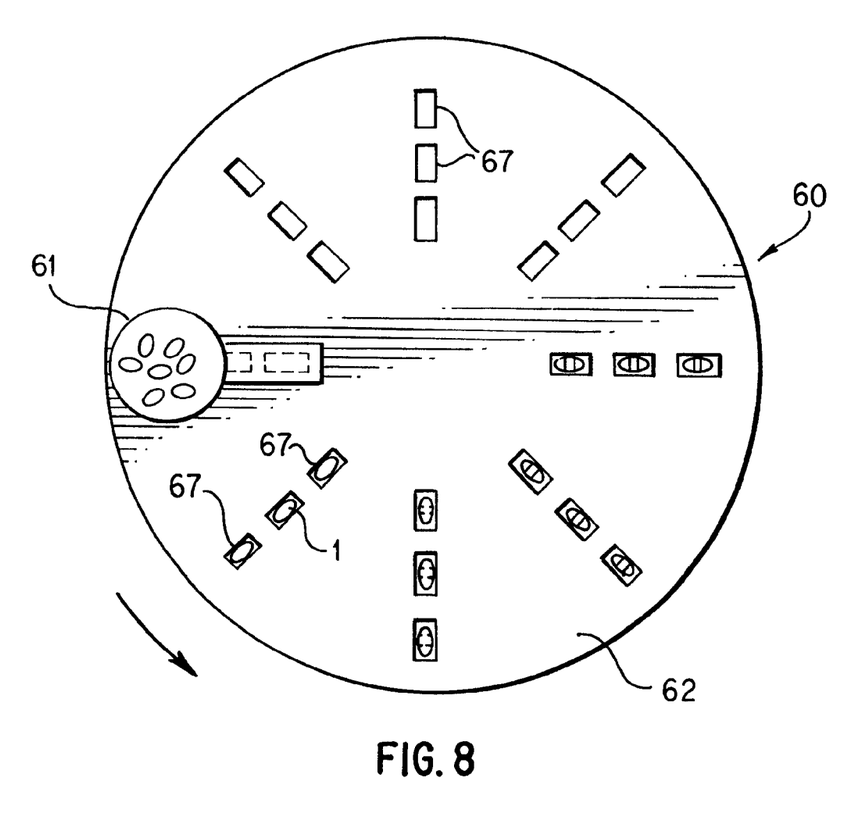
FIG. 8 is a top view of the banding system illustrated in FIG. 7, the tablet drying means not being shown.

Located above table 62 is a drying apparatus, indicated generally as 69. Drying apparatus 69 may be of conventional design, including, for example, a fan for forcing ambient air over a heater element to warm the air, which is then directed with appropriate ducting to the area of table 62 in which banded tablets are located. The banded tablets will continue to rotate because of the rotation of table 62 over stationary table 63 and be dried as they pass through the warm-air environment provided by the drying apparatus 69. While a single drying apparatus at a single drying station is shown, it will be understood that multiple units may be used if necessary to complete the drying of the banded tablets in a single cycle of rotation of table 62. In some circumstances, particularly, where relatively thicker bands are deposited on the blanks, a first drying apparatus may provide an initial amount of drying at a lower temperature to prevent too rapid drying of the banding material, and one or more additional drying apparatuses may provide additional drying cycles at a higher temperature to complete final drying of the banded tablets.

Table 63 is formed with a second set of openings or a continuous slot (not shown) extending along a radius of table 63 through which banded tablets may be released from the slots 67 into a collection apparatus.

As table 62 rotates above the stationary surface of table 63, the blanks rotate about their longitudinal axes as they are transported to the banding station. Although only a single printing wheel 66 is shown for illustration purposes, it is to be understood that a plurality of printing wheels may be provided along a radius of table 62 under openings 67 so that each blank will be appropriately banded as it reaches the banding station. In that manner, each of the blanks positioned within openings 67 along a particular radius of table 62 may be banded at the same time. In those instances where blanks having a plurality of grooves are to be banded, it will usually be most efficient to provide multiple printing wheels equal to the number of grooves at each banding station so that each of the grooves may be banded simultaneously. If it is desired, a similar banding station may be positioned at another set of openings 67 in table 63 along other radii, thus providing the opportunity to apply additional banding material to the banded blanks if thicker coatings or coatings of different compositions are desired.

Figure 9:
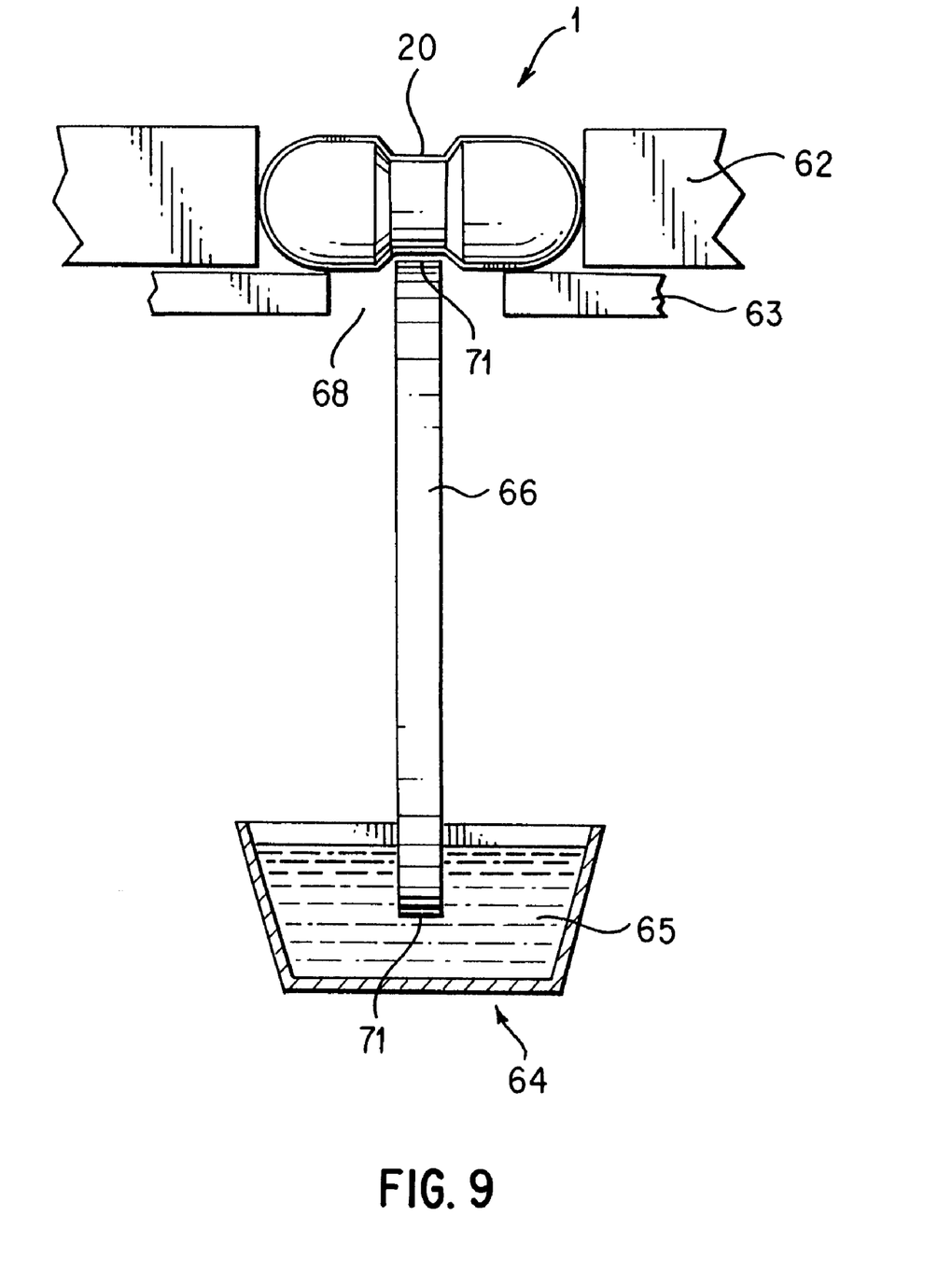
FIG. 9 is an illustration of one embodiment of the printing station in the banding means of the invention with a printing wheel having a substantially planar printing surface.
Figure 10:
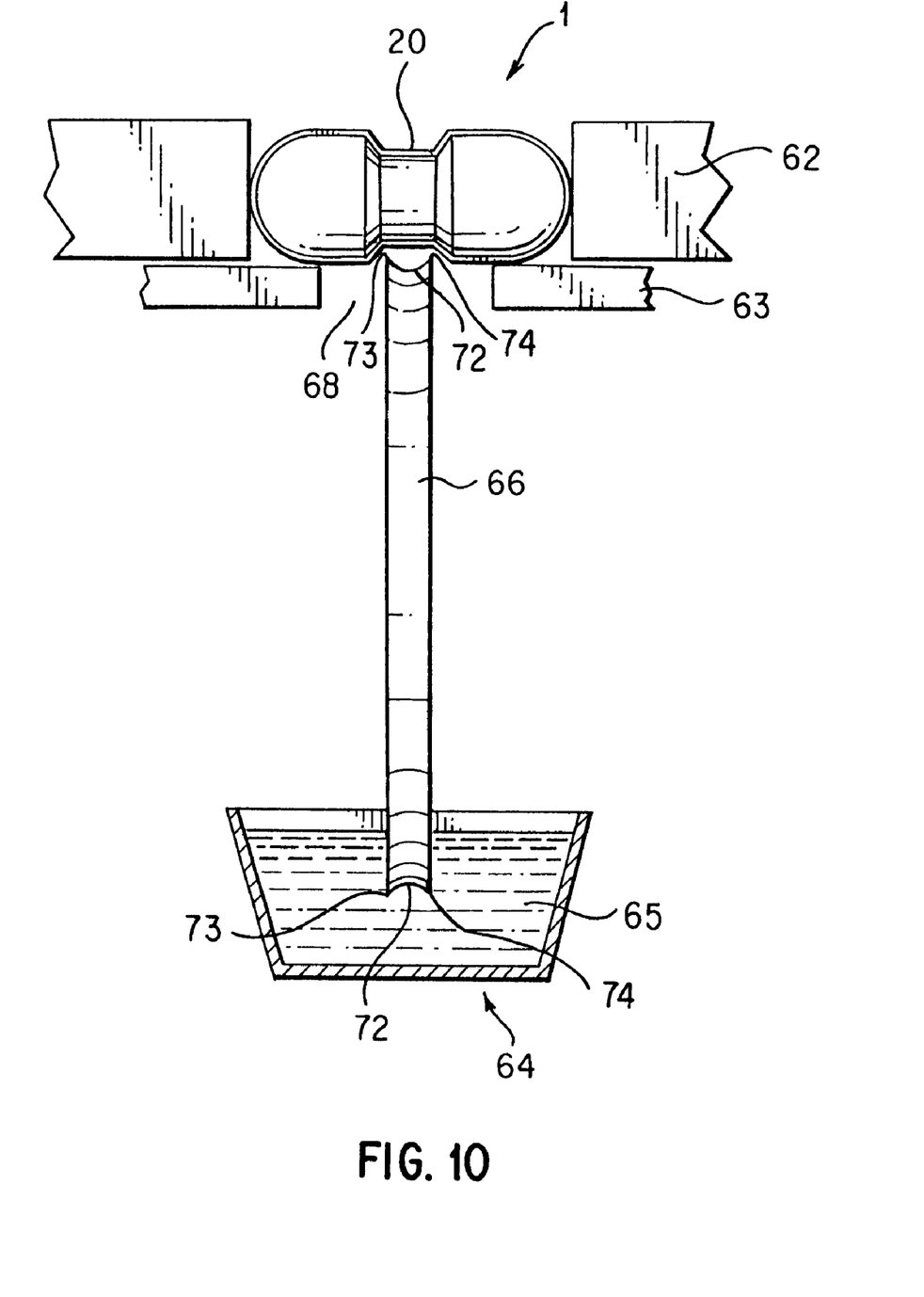
FIG. 10 is an illustration of an alternate embodiment of the printing station in the banding means of the invention with a printing wheel having a concave printing surface.

As shown in FIGS. 9 and 10, the grooves formed on the blanks of the invention act as an indexing or register means to cooperate with the printing means in the fabrication system and at the same time provide dispensing devices having the desired release profile of active agent. With reference to FIG. 9, blank 1 is shown at a location above a printing wheel 66. Groove 20 is indexed by and registers with banding wheel 66. The outer circumferential surface of banding wheel 66 may be a generally planar surface 71 as shown in FIG. 9, or it may be a concave surface 72 as shown in FIG. 10. The concave surface is usually employed if thicker bands are required to obtain the desired release profile of the active agent, since the concave surface permits the application of a greater mass of banding material in a single application than is possible with the flat surface. The printing surface of printing wheel 66 may optionally be smooth or rough depending upon the application intended. A rough surface can consist of a knurled surface, a sandblasted or pebbled surface, or a matte finish. The purpose of the roughened printing surface is to promote frictional contact to the blank as the blank rotates over printing wheel 66 to enhance rotation with improved traction. Another purpose of the roughened surface is to increase the application rate of banding material 65 by increasing the amount of banding material transferred from the band feed source per each rotation of the printing wheel. The printing surface of the printing wheel can also be configured with one or more channels to facilitate efficient transfer of the banding material from the feed source to the blank. An end-on view of such a printing wheel with a single channel 72 is illustrated in FIG. 10. The edges 73 and 74 forming the channel may be smooth or roughed as discussed previously with respect to the planar surface of printing wheel 66. As printing wheel 66 rotates through the banding material, it picks up banding material on its circumferential surface and deposits it onto the surface of groove 20. The rate of rotation of table 62 is adjusted to provide a residence time for the blanks at the banding station that is adequate to allow for application of the desired amount of banding material. Typically, table 62 will rotate in a range of 0.25 to 2.1 revolutions per minute (rpm) and printing wheel 66 will rotate in a range of 15 to 120 rpm. For most typical applications, table 62 preferably rotates between 0.5 and 0.75 rpm, most preferably between 0.6 and 0.7 rpm, and printing wheel 66 preferably rotates between 30 and 60 rpm, most preferably between 40–50 rpm.

The grooves in the blanks additionally act as templates for the formation of bands on the dosage forms, thus facilitating control of the width, depth, location and edge characteristics of the bands. Also, banded dosage forms having a smooth, outer surface can be produced with or without coating of an overlayer on the banded tablet.

Fabrication of expandable dosage forms, for example, those intended for gastric retention, follows a similar procedure. In this case, the groove which circumscribes the tablet may be either shallow or deep. However, if the dosage form is intended to expand significantly from uptake of fluid (e.g. 100% to 500% of its dry volume), deeper grooves usually will be employed. In the deep-groove configuration, the shape of the groove can be in the form of a notch or a saddle point (FIGS. 3–6). The diameter of the tablet at these deep-grooved areas is smaller than the tablet diameter overall. Therefore, when this core is banded at a fixed wheel rotation speed and fixed dwell time, a thicker band can form within the groove than would be formed without the groove. Thick, robust rings are needed when the gastric retention system is in operation to withstand the pressure generated by high-swelling fibers and hydrogels of the core as the system enlarges to dimensions larger than the pylorus. Typically, deep-grooved rings will have a maximum depth of from about 0.5 mm to about 3 mm, although it is understood that the thickness may be less or greater as selected by one skilled in the art for the particular application at hand.

Figure 11:
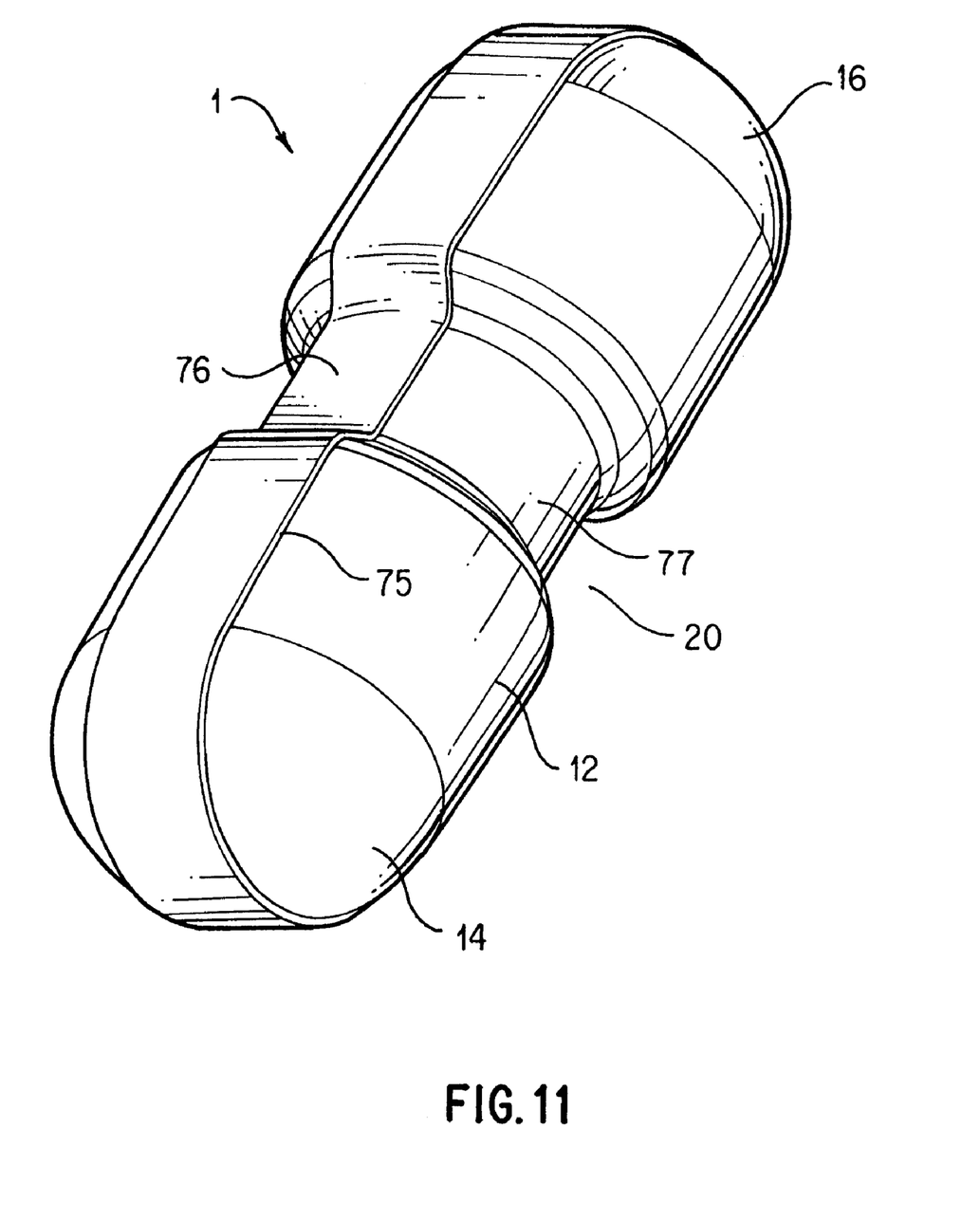
FIG. 11 is a perspective view of a typical blank of this invention formed from horizontal compression in a tabletting press.

FIG. 11 illustrates a typical blank 1 formed with a groove 20 from horizontal compression of the bulk active agent formulation. In contrast to conventional gelatin capsules that have a smooth outer surface and are generally of circular cross-section, a horizontally compressed blank may have a number of surfaces, such as the land area designated 75 and surfaces 76 and 77, that impart some non-circular irregularity to the cross-section of the tablet. Application of the banding material according to the process of the present invention typically will cover those surfaces with banding material to provide a smooth surface after banding. To the extent that the land area outside of the groove is not covered by banding material, the banded tablet may be overcoated as described previously to provide for a smooth, outer surface.

The active agent of the active agent formulation may be in liquid, solid or semisolid form. The active agent formulation may contain additional materials and may be designed in a multitude of ways to provide a specific drug delivery profile. One embodiment comprises a formulation that contains a biologically acceptable hydrophilic polymer which is capable of slow dispersion in the environmental fluid. In another embodiment, the formulation may contain a hydrophilic polymer and a surfactant so that the formulation is susceptible to erosion in the environment. In still another embodiment, the formulation may include a solid surfactant so that the formulation is susceptible to erosion in the environment. In still another embodiment, the formulation may include a solid surfactant and provide drug delivery in a finely dispersed form. In yet a further embodiment, the formulation may include coated microspheres of an active agent and an adjuvant. The active agent and adjuvant can be delivered simultaneously from the microspheres either by diffusion or by osmosis. Suitable materials useful as active agent carriers and excipients are known in the art and are disclosed in U.S. Pat. Nos. 4,595,583 and 4,874,388, for example.

The terms "active agent" and "drug" are used interchangeably herein and refer to an agent, drug, compound, composition of matter or mixture thereof which provides some pharmacologic, often beneficial, effect. This includes pesticides, herbicides, germicides, biocides, algicides, rodenticides, fungicides, insecticides, antioxidants, plant growth promoters, plant growth inhibitors, preservatives, antipreservatives, disinfectants, sterilization agents, catalysts, chemical reactants, fermentation agents, foods, food supplements, nutrients, cosmetics, drugs, vitamins, sex sterilants, fertility inhibitors, fertility promoters, microorganism attenuators and other agents that benefit the environment of use. As used herein, the terms further include any physiologically or pharmacologically active substance that produces a localized or systemic effect or effects in animals, including warm blooded mammals, humans and primates; avians; domestic household or farm animals such as cats, dogs, sheep, goats, cattle, horses and pigs; laboratory animals such as mice, rats and guinea pigs; fish; reptiles; zoo and wild animals; and the like. The active drug that can be delivered includes inorganic and organic compounds, including, without limitation, drugs which act on the peripheral nerves, adrenergic receptors, cholinergic receptors, the skeletal muscles, the cardiovascular system, smooth muscles, the blood circulatory system, synoptic sites, neuroeffector junctional sites, endocrine and hormone systems, the immune system, the reproductive system, the skeletal system, autacoid systems, the alimentary and excretory systems, the histamine system and the central nervous system. Suitable agents may be selected from, for example, proteins, enzymes, hormones, polynucleotides, nucleoproteins, polysaccharides, glycoproteins, lipoproteins, polypeptides, steroids, hypnotics and sedatives, psychic energizers, tranquilizers, anticonvulsants, muscle relaxants, antiparkinson agents, analgesics, antiepileptics, antibiotics, anti-inflammatories, local anesthetics, muscle contractants, antimicrobials, antivirals, antimalarials, hormonal agents including contraceptives, sympathomimetics, polypeptides and proteins capable of eliciting physiological effects, diuretics, lipid regulating agents, antiandrogenic agents, anfiparasitics, neoplastics, antineoplastics, hypoglycemics, nutrional agents and supplements, growth supplements, fats, ophthalmics, antienteritis agents, electrolytes and diagnostic agents.

Examples of beneficial agents useful in this invention include prochlorperazine edisylate, ferrous sulfate, aminocaproic acid, mecamylamine hydrochloride, procainamide hydrochloride, amphetamine sulfate, methamphetamine hydrochloride, benzphetamine hydrochloride, isoproterenol sulfate, phenmetrazine hydrochloride, bethanechol chloride, methacholine chloride, pilocarpine hydrochloride, atropine sulfate, scopolamine bromide, isopropamide iodide, tridihexethyl chloride, phenformin hydrochloride, methylphenidate hydrochloride, theophylline cholinate, cephalexin hydrochloride, diphenidol, meclizine hydrochloride, prochlorperazine maleate, phenoxybenzamine, thiethylperazine maleate, anisindione, diphenadione erythrityl tetranitrate, digoxin, isoflurophate, acetazolamide, methazolamide, bendroflumethiazide, phenytoin, minocycline, acyclovir, ganciclovir, fenoxadine, chlorpropamide, tolazamide, chlormadinone acetate, phenaglycodol, allopurinol, aluminum aspirin, fexofenadine, methotrexate, acetyl sulfisoxazole, hydrocortisone, hydrocorticosterone acetate, cortisone acetate, dexamethasone and its derivatives such as betamethasone, triamcinolone, methyltestosterone, 17-β-estradiol, ethinyl estradiol, ethinyl estradiol 3-methyl ether, prednisolone, 17-β-hydroxyprogesterone acetate, 19-norprogesterone, norgestrel, norethindrone, norethisterone, norethiederone, progesterone, norgesterone, norethynodrel, aspirin, acetaminophen, indomethacin, naproxen, fenoprofen, sulindac, indoprofen, nitroglycerin, isosorbide dinitrate, propranolol, timolol, atenolol, alprenolol, cimetidine, clonidine, imipramine, levodopa, chlorpromazine, methyidopa, dihydroxyphenylalanine, calcium gluconate, ketoprofen, ibuprofen, cephalexin, erythromycin, haloperidol, zomepirac, ferrous lactate, vincamine, phenoxybenzamine, diltiazem, milrinone, captropril, mandol, quanbenz, hydrochlorothiazide, ranitidine, flurbiprofen, fenbufen, fluprofen, tolmetin, alclofenac, mefenamic, flufenamic, difuninal, nimodipine, nitrendipine, nisoldipine, nicardipine, felodipine, lidoflazine, tiapamil, gallopamil, amlodipine, mioflazine, lisinopril, enalapril, captopril, ramipril, enalaprilat, famotidine, nizatidine, sucralfate, etintidine, tetratolol, minoxidil, chlordiazepoxide, diazepam, amitriptyline, and imipramine. Further examples are proteins and peptides which include, but are not limited to, insulin, colchicine, glucagon, thyroid stimulating hormone, parathyroid and pituitary hormones, calcitonin, renin, prolactin, corticotrophin, thyrotropic hormone, follicle stimulating hormone, chorionic gonadotropin, gonadotropin releasing hormone, bovine somatotropin, porcine somatropin, oxytocin, vasopressin, prolactin, somatostatin, lypressin, pancreazymin, luteinizing hormone, LHRH, interferons, interleukins, growth hormones such as human growth hormone, bovine growth hormone and porcine growth hormone, fertility inhibitors such as the prostaglandins, fertility promoters, growth factors, and human pancreas hormone releasing factor.

It is to be understood that more than one active agent may be incorporated into the active agent formulation in a device of this invention, and that the use of the term "agent" or "drug" in no way excludes the use of two or more such agents or drugs.

The agents can be in various forms, such as uncharged molecules, components of molecular complexes or nonirritating, pharmacologically acceptable salts. Also, simple derivatives of the agents (such as ethers, esters, amides, etc) which are easily hydrolyzed by body pH, enzymes, etc, can be employed.

The amount of active agent employed in the delivery device will be that amount necessary to deliver a therapeutically effective amount of the agent to achieve the desired result at the site of delivery. In practice, this will vary widely depending upon the particular agent, the site of delivery, the severity of the condition, and the desired therapeutic effect. Thus, it is not practical to define a particular range for the therapeutically effective amount of active agent incorporated into the device.

The hydrophilic polymeric material useful herein may comprise, polysaccharides, methyl cellulose, sodium or calcium carboxymethyl cellulose, nitrocellulose, carboxymethyl cellulose and other cellulose ethers, and polyethylene oxides (e.g., Polyox®, Union Carbide). Other materials useful as the hydrophilic polymeric material include but are not limited to hydroxypropyl cellulose, low-substituted hydroxypropyl cellulose, hydroxypropyl methyl cellulose, hydroxyethyl cellulose, methyl ethyl cellulose, ethylhydroxy ethylcellulose, cellulose acetate, cellulose butyrate, cellulose propionate, cellulose fibers, gelatin, collagen, starch, maltodextrin, pullulan, polyvinyl pyrrolidone, polyvinyl alcohol, polyvinyl acetate, glycerol fatty acid esters, polyacrylamide, polyacrylic acid, sodium and potassium salts of polyacrylic acid, copolymers of ethacrylic acid or methacrylic acid (Eudragit™) or other acrylic acid derivatives, sorbitan esters, natural gums, lecithins, pectin, alginates, ammonia alginate, sodium or potassium alginate, calcium alginate, propylene glycol alginate, potassium alginate, agar, gum arabic, gum karaya, locust bean gum, gum tragacanth, carrageenans, gum ghatti, guar gum, xanthan gum, scleroglucan, and blends of the above.

The pharmaceutically acceptable carrier useful herein may comprise more than one ingredient, such as, for example, a buffer, a viscosity regulating vehicle, a surfactant, a dye, a permeation enhancer, a proteinase inhibitor, or other formulation ingredients and additives, as are known in the art.

The rate of release of the active agent from the active agent dosage forms is predominantly controlled by erosion of the aqueous gel formed by contacting the matrix with the fluid environment of use.

The rate of active agent released from a cylindrical dosage form without bands versus time will continuously decrease with time. As drug is released from an unbanded capsule, the diameter of the cylinder as well as the area of erosion decreases. In contrast, as the polymeric core of the banded cylinder of this invention shrinks, new surface area is created and exposed to the environment of use as described in greater detail in the '263 patent. As a result, the amount of active agent released over time may remain constant or may increase with time depending on the rate of the new surface area being generated. By arrangement of the number, size and location of bands on the dosage form, the total new surface area created by erosion can be predicted and the desired release profile can be achieved.

The bands may be placed onto the surface of the matrix such that, as the matrix erodes, the bands become loose and drop off the matrix. These bands are easily excreted from the gastrointestinal tract. As the number of bands remaining on the surface of the matrix decreases, more matrix surface area will be exposed. The matrix will therefore erode in a fashion that approaches zero order rate.

In order to prepare a device of the present invention, the active agent formulation is first prepared and formed into a blank of the desired size and shape and having the desired number of grooves with the desired groove shape. The matrix in its initial prepared form is about the size and dimensions of a size "5" to size "000" hard gelatin capsule.

The cross-sectional shape of the matrix may be circular or may be oval or other shapes that are able to be manipulated by the banding system, indexed by means of the grooves acting as registers and printed. Generally, shapes that are easily rotated by the printing wheel of the systems described herein, e.g., circular and oval, will be most preferred.

The following examples are illustrative of the present invention. They are not to be construed as limiting the scope of the invention. Variations and equivalents of these examples will be apparent to those skilled in the art in light of the present disclosure, the drawings and the claims herein.

EXAMPLE 1

A delivery device according to the present invention is prepared as follows. 580 grams of the analgesic drug, ibuprofen, 250 grams of hydroxypropyl methylcellulose having a number average molecular weight of 9,200 grams per mole, and 150 grams of hydroxypropyl methylcellulose having a molecular weight of 242,000 grams per mole, is passed through a screen having a mesh size of 40 wires per inch. The cellulose each have an average hydroxyl content of 8 weight percent and an average methoxyl content of 22 weight percent. The resulting sized powders are tumble mixed. Anhydrous ethyl alcohol is added slowly to the mixed powders with stirring until a dough consistency is produced. The damp mass is then extruded through a 20 mesh screen and air dried overnight. The resulting dried material is re-screened through a 20 mesh screen to form the final granules. 2 grams of the tabletting lubricant, magnesium stearate, which has been sized through an 80 mesh screen, is then tumbled into the granules.

690 mg of the resulting granulation is placed in a die cavity formed with three, uniformly spaced convex ridges, each having a semi-circular cross-sectional shape and a height of 0.7 mm. The inside dimensions of the die, not including the ridged areas, are 15 mm by 9 mm. The granulation is horizontally compressed with deep concave punch tooling using a punch formed with ridges on its interior surface that correspond to the ridges in the die to form complementary groove when the compression operation is completed. Compression takes place at a pressure head of 2 tons. This forms a longitudinal blank having an overall length, including the rounded ends, of 15 mm and a concave groove with a depth of 0.7 mm. The cylindrical body of the blank, from tablet land to tablet land, spans a distance of 9 mm. Each blank contains a unit dose of drug of 400 mg. The capsules are fed into a Tait Capsealer Machine (Tait Design and Machine Co., Manheim, Pa.), modified as described herein, where the rotating printing wheels engage the grooves and align the blank for the printing operation. Three bands are printed onto each capsule. The material forming the bands is a mixture of 50 wt % ethylcellulose dispersion (Surelease®, Colorcon, West Point, Pa.) and 50 wt % ethyl acrylate methylmethacrylate (Eudragit® NE 30D, RöhmPharma, Weiterstadt, Germany). The bands are applied as an aqueous dispersion and the excess water is driven off in a current of warm air. The diameter of the bands is 2 millimeters. The finished dosage form has a smooth outer surface and delivers ibuprofen over a prolonged period of time.

Drug release studies are performed by placing the dosage forms in a slotted basket. The inside diameter of the basket is 14 mm and the length is 50 mm. The basket is attached to a reciprocating motor. The basket is then immersed in 50 ml of simulated intestinal fluid at 37° C., and shaken vertically in the media with a amplitude of 3.8 cm and a frequency of 99–101 cycles per minute. After 1 hour of shaking, the basket is transferred to a fresh 50 ml volume of the test media. This procedure is continued, hour by hour, for nine hours. The systems then are allowed to release continuously for another 13 hours to complete a 24 hour test duration. The release receptor solutions are then analyzed for drug content by ultraviolet spectroscopy. The release rate as a function of time and cumulative release as a function of time are computed. The delivery devices of the invention release active agent over a prolonged period of time.

EXAMPLE 2

A blank with the ibuprofen matrix formulation described in Example 1 is formed with one notched groove having sloping side wall at an angle of 30 degrees with the longitudinal axis of the tablet and banded with one band. The resulting dosage form has a substantially smooth outer surface, with the edges and thickness of the bands being substantially uniform. The dosage form delivers ibuprofen over a prolonged period.

EXAMPLE 3

A fast-release drug granulation is prepared as follows; 870 grams of ibuprofen, 100 grams of hydroxypropyl cellulose having a hydroxypropoxyl content of 11 weight percent, and 10 grams of hydroxypropyl methyl cellulose having a hydroxypropoxyl content of 8 weight percent and a methoxy content of 22 weight percent and having a number average molecular weight of 9,200 grams per mole, are screened through a 40 mesh sieve. The sized powders are mixed and anhydrous ethanol is added with stirring until a uniform, damp mass is produced. The mixture is extruded through a 20 mesh sieve. The elongated granules produced are air dried. The dried granules are rescreened through a 20 mesh sieve. 20 Grams of stearic acid which has been passed through an 80 mesh sieve are tumble mixed into the granules for 3 minutes. 690 mg of the granulation of Example 1 is filled into a die cavity having two semicircular ridges with sides at an angle of 30 degrees with the longitudinal axis of the die and an inside diameter in an area not including the ridges of 6 mm and horizontally lightly compressed with deep concave punch tooling. The upper punch is removed and 230 mg of the fast-release granulation is placed on the lightly compressed core. A second upper punch, formed with two ridges that cooperate with the ridges in the die to create the two grooves in the blank, is placed in the die cavity and a 2 ton compression force is applied, thereby forming a two-layered tablet. Two rings are printed onto the dosage form according to the procedures herein.

An abrasion resistant, protective coating is applied to the banded, two-layered tablet as follows. A coating solution is prepared by dissolving 63 grams of hydroxypropyl methylcellulose having a hydroxypropoxyl content of 10 weight percent and a methoxy content of 29 weight percent with a number average molecular weight of 11,900 grams per mole, and 7 grams of polyethylene glycol having a molecular weight of 3,350 grams per mole, in 930 grams of water. The banded dosage form is then placed in a pan coating machine. The coating solution is sprayed onto the banded tablet in a current of warmed air until 40 mg of film are deposited on each tablet.

The resulting two-layer, film coated system releases a portion of ibuprofen rapidly and a portion of ibuprofen over a prolonged period.

The above description has been given for ease of understanding only. No unnecessary limitations should be understood therefrom, as modifications will be obvious to those skilled in the art.

What is claimed is:

1. A method of preparing an active agent dosage form for the prolonged delivery of the active agent, comprising:
    forming a blank from an active agent formulation matrix so that the blank has a groove circumscribing a portion of the external surface of the blank; and
    depositing insoluble material in the groove.

2. The method of claim 1, wherein said forming step comprises:
    compressing the active agent formulation matrix; and
    embossing the groove in the active agent formulation matrix so that it lies in a plane perpendicular to the longitudinal axis of the blank.

3. The method of claim 1, wherein said depositing step comprises:
    using printing means to transfer insoluble material into the groove.

4. The method of claim 3, wherein the printing means comprises a rotatable wheel.

5. The method of claim 4, wherein the wheel has a substantially planar outer circumferential surface.

6. The method of claim 4, wherein the wheel has a concave outer circumferential surface.

7. The method of claim 1, wherein said depositing step is carried out so that the insoluble material does not extend above the external surface of the blank.

8. The method of claim 1, further comprising:
    coating the blank with a water-soluble film.

9. A method for fabricating an active agent dosage form for the prolonged delivery of the active agent, comprising:
    providing a blank, the blank comprising an active agent formulation matrix having a groove circumscribing a portion of the external surface of the blank;
    orienting the blank with respect to a forming means for forming an insoluble band in the groove, said orienting comprising registering the forming means with the groove; and
    forming the insoluble band in the groove using the forming means.

10. The method of claim 9, wherein said registering step is carried out using a rotatable wheel.

11. The method of claim 9, wherein said forming step comprises:
    using printing means to transfer insoluble material into the groove.

12. The method of claim 11, wherein the printing means comprises a rotatable wheel.

13. The method of claim 12, wherein the wheel has a substantially planar outer circumferential surface.

14. The method of claim 12, wherein the wheel has a concave outer circumferential surface.

15. The method of claim 9, wherein said forming step is carried out so that the band does not extend above the external surface of the blank.

16. The method of claim 9, further comprising:
    coating the blank with a water-soluble film.

17. The method of claim 9, further comprising:
    transporting the blank from a source of blanks to the forming means.

18. An active agent dosage form for the prolonged delivery of an active agent formulation to a fluid environment of use, comprising:

an active agent formulation matrix having a groove circumscribing a portion of the external surface thereof; and an insoluble band disposed in said groove.

19. The active agent dosage form of claim 18, wherein said groove has a notch shape.

20. The active agent dosage form of claim 18, wherein said groove has a concave shape.

21. The active agent dosage form of claim 18, wherein the depth of said groove is between about 0.1 mm and about 3 mm.

22. The active agent dosage form of claim 18, wherein the width of said groove is between about 0.5 mm and 10 mm.

23. The active agent dosage form of claim 18, further comprising:

a water-soluble film coating.

24. The active agent dosage form of claim 18, wherein the dosage form comprises a plurality of grooves, each of said grooves circumscribing a portion of the external surface of the active agent formulation matrix.

25. The active agent dosage form of claim 24, wherein the dosage form comprises an insoluble band disposed in each of said grooves.

26. The active agent dosage form of claim 18, wherein said insoluble band comprises a latex of acrylate polymers.

27. The active agent dosage form of claim 26, wherein said acrylate polymers comprise copolymers of ethylacrylate and methylmethacrylate.

28. The active agent dosage form of claim 26, wherein said latex comprises an ethylacrylate methylmethacrylate 2:1 copolymer latex.

29. The active agent dosage form of claim 18, wherein said active agent formulation matrix has a cylindrical shape.

30. The active agent dosage form of claim 29, wherein each end of said active agent formulation matrix is rounded and convex.

* * * * *